(12) United States Patent  (10) Patent No.: US 8,933,293 B2
De Bruin et al.  (45) Date of Patent: Jan. 13, 2015

(54) GRAPHICS PERFORMANCE IN DIFFERENT ABSORBENT ARTICLE CONSTRUCTIONS

(75) Inventors: Paula K. De Bruin, Sherwood, WI (US); Donald Joseph Osentoski, Menasha, WI (US); Tom Michael Ales, III, Neenah, WI (US); Marcille Faye Ruman, Oshkosh, WI (US); Joy Patricia Bauman, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 435 days.

(21) Appl. No.: 13/374,159

(22) Filed: Dec. 14, 2011

(65) Prior Publication Data

US 2013/0158493 A1  Jun. 20, 2013

(51) Int. Cl.
*A61F 13/15*  (2006.01)
*B32B 38/14*  (2006.01)

(52) U.S. Cl.
USPC ............ 604/361; 604/359; 604/362; 156/277

(58) Field of Classification Search
USPC ......................................... 604/361, 359, 362
See application file for complete search history.

(56) References Cited

U.S. PATENT DOCUMENTS

| | | | |
|---|---|---|---|
| 5,197,958 A * | 3/1993 | Howell | 604/361 |
| 6,297,424 B1 | 10/2001 | Olson et al. | |
| 6,635,797 B2 | 10/2003 | Olson et al. | |
| 6,710,221 B1 | 3/2004 | Pierce et al. | |
| 7,718,844 B2 | 5/2010 | Olson | |
| 2002/0007162 A1 | 1/2002 | Cammarota et al. | |
| 2004/0064113 A1 | 4/2004 | Erdman | |
| 2004/0108054 A1 | 6/2004 | Otsubo et al. | |
| 2005/0067083 A1 | 3/2005 | Vergona | |
| 2005/0124954 A1 | 6/2005 | Adams et al. | |
| 2005/0234414 A1 | 10/2005 | Liu | |
| 2006/0020249 A1 | 1/2006 | Allen | |
| 2006/0069362 A1 | 3/2006 | Odorzynski et al. | |
| 2006/0149197 A1 | 7/2006 | Niemeyer | |
| 2006/0173428 A1 | 8/2006 | Acors | |
| 2006/0224132 A1 | 10/2006 | Roe et al. | |
| 2006/0264858 A1 | 11/2006 | Roe et al. | |
| 2007/0207295 A1 | 9/2007 | Lu | |
| 2008/0132872 A1 | 6/2008 | Trennepohl et al. | |
| 2008/0195072 A1 | 8/2008 | Warner | |
| 2009/0062757 A1 | 3/2009 | Long et al. | |
| 2009/0247979 A1 | 10/2009 | Sosalla et al. | |
| 2009/0287173 A1 | 11/2009 | Sosalla et al. | |
| 2010/0030173 A1 | 2/2010 | Song et al. | |
| 2010/0089264 A1 | 4/2010 | Warner | |
| 2010/0168700 A1 | 7/2010 | Schmidt et al. | |
| 2011/0137274 A1 | 6/2011 | Klofta et al. | |
| 2011/0144603 A1 | 6/2011 | Song | |

* cited by examiner

*Primary Examiner* — Jacqueline F. Stephens
(74) *Attorney, Agent, or Firm* — Kimberly-Clark Worldwide, Inc.

(57) ABSTRACT

The invention relates to a multiple layer material that includes a film layer, a moisture-reacting composition layer and an adhesive layer. The film layer has at least one printed surface. The moisture-reacting composition layer is adjacent the printed surface of the film layer. A portion of the moisture-reacting composition layer forms a framing device. The adhesive layer is adjacent the portion of the moisture-reacting composition layer forming the framing device. The multiple layer material of the invention may be used to form a component of an absorbent article having active graphics that change in appearance in response to moisture.

6 Claims, 3 Drawing Sheets
(2 of 3 Drawing Sheet(s) Filed in Color)

GRAPHICS PERFORMANCE IN DIFFERENT ABSORBENT ARTICLE CONSTRUCTIONS

FIELD OF THE INVENTION

The present invention relates to a multiple layer material that includes a film layer, a moisture-reacting composition layer and an adhesive layer. The film layer has at least one printed surface. The moisture-reacting composition layer is adjacent the printed surface of the film layer. A portion of the moisture-reacting composition layer forms a framing device. The adhesive layer is adjacent the portion of the moisture-reacting composition layer that forms the framing device. The multiple layer material of the invention may be used to form one or more components of an absorbent article, such as the outer cover of an absorbent article. The moisture-reacting composition layer may be formed in such a way as to create an aesthetically-pleasing graphic that is responsive to the presence of moisture in the absorbent article (an active graphic that changes appearance in response to the presence of moisture). The intensity of the change in appearance of the moisture-reacting composition layer can be adjusted based on the placement of other components in the absorbent article and how the adhesive layer is applied to the moisture-reacting composition layer.

BACKGROUND OF THE INVENTION

Many different types of absorbent products exist that are designed to be worn or otherwise associated with the body for absorbing body fluids. Such absorbent products can include, but are not limited to, diapers, training pants, adult incontinence products, feminine hygiene products, bed liners, bandages, and the like. In some aspects, the absorbent articles contain an outer cover, a liner and an absorbent structure positioned in between the outer cover and the liner. In addition to these foundational functional components of absorbent articles, it is well known in the art to incorporate graphics into such absorbent articles. Graphics may be incorporated into one or more of the functional components. Additionally, the incorporated graphics may serve one or more purposes: aesthetic appeal, toilet-training aid, extent of product usage and physiological state of the wearer of the article. The absorbent structure typically contains superabsorbent particles. Many absorbent articles, especially those sold under the trade name HUGGIES by the Kimberly-Clark Corporation, are so efficient at absorbing liquids that it is sometimes difficult for the wearer or the caregiver to tell whether or not the absorbent article has been insulted with a body fluid, such as urine.

Accordingly, various types of moisture or wetness indicators have been suggested for use in absorbent articles. The wetness indicators can be used for different purposes. For instance, the wetness indicators can be designed to assist parents or attendants by helping them identify a wet diaper condition early on.

Wetness indicators can also be used as a training aid for small children during the toilet training process. For example, wetness indicators can be designed to discourage small children from wetting the absorbent article and to encourage small children to use a toilet like an adult.

Wetness indicators used in the past have included wetness indicator graphics that have been printed on the absorbent article. Absorbent articles having wetness indicator graphics, for instance, are described in U.S. Pat. No. 6,297,424; in U.S. Pat. No. 6,710,221; and in U.S. Patent Application Publication No. 2006/0149197, which are all incorporated herein by reference. Although the above patents have provided great advances in the art, further improvements are still needed.

For instance, prior commercial wetness indicator graphics have been created using moisture-responsive inks that dissolve when wet. The graphics are created using moisture-responsive inks that are printed onto one or more components of the absorbent article. For example, the outer cover component may be formed of a laminate of a breathable, but moisture barrier film and a nonwoven material. Graphics may be formed by printing on one or both sides of the moisture barrier film. The other components of the absorbent article, such as the liner and the absorbent structure, may also be printed with moisture-responsive inks to form the graphics. In some instances, once contacted with urine, the graphics smear and fade indicating that the absorbent article is wet. Unfortunately, however, graphics produced with moisture-responsive inks have been somewhat limited in size, shape, position, line width, color and the like in order to ensure sufficient fading when contacted with urine. The location of the moisture-responsive ink within the construction of the absorbent article impacts the aesthetic performance of the ink. For example, if the moisture-responsive ink is not readily exposed to moisture accumulating in the absorbent structure, the graphic printed with the moisture-responsive ink may only partially change in appearance. In addition to not providing a clear indication of product usage, a partially faded or blurred appearance may detract from the overall appearance of the absorbent article.

Other components of the absorbent article have been found to interfere with the performance (e.g. definition of the graphic fade, completeness of the graphic fade, aesthetic appearance of the graphic fade, etc.) of the moisture-responsive inks. For example, construction adhesive is believed to interfere with the performance of moisture-responsive inks. For example, if construction adhesive is applied over the moisture-responsive ink, the construction adhesive will interfere with the ability of the moisture-responsive ink to change in appearance in response to the presence of moisture. If the moisture-responsive ink is printed on the inward-facing surface of the outer cover component, article components placed between the outer cover component and the absorbent structure may interfere with the performance of the moisture-responsive ink. For example, some absorbent article constructions include a tissue layer or spacer layer between the absorbent structure and the outer cover component. It is believed that the tissue layer/spacer layer may interfere with the performance of the moisture-responsive ink. For example, such layers may interfere with how completely the ink changes in appearance in response to moisture being present. If the moisture-responsive ink "disappears" in response to the presence of moisture, the tissue layer/spacer layer may interfere with the ability of the graphic to fade and disappear in response to moisture. If the moisture-responsive ink changes color in response to the presence of moisture, the tissue layer/spacer layer may interfere with the ability of the graphic to clearly and completely change color in response to moisture.

In some instances, it is desirable for the moisture-responsive ink to change in appearance within a "framed" area of a component of an absorbent article. Examples of absorbent articles having an active graphic with a framing device surrounding the active graphic are described in U.S. patent application Ser. No. 12/852,192 filed on Aug. 6, 2010. When the moisture-responsive ink has to change in appearance within a framed area, it is desirable for the change to be distinctive and to be complete across the entirety of the framed area. Given the general construction of absorbent articles, currently-available moisture-responsive inks and the objective of an aesthetically-appealing article, there remains a need for absorbent articles utilizing moisture-responsive inks to provide dramatic changes in appearance in response to the presence of moisture. There also remains a need to leverage the other components of the absorbent article to improve the performance of the moisture-responsive ink.

SUMMARY

In one aspect, the present invention relates to a multiple layer material, such as could be used to form the outer cover or outer layer of an absorbent article; the multiple layer material includes a moisture-reacting composition layer that can be used to form a graphic image for aesthetic or functional purposes. The present invention also relates to a multiple layer material that includes a film layer with a printed surface; adjacent the film layer are a leuco dye-based composition layer and a water-soluble ink composition layer, both of which form a graphic element. In another aspect, the present invention relates to a method of forming a gradient effect graphic for an absorbent article; the novel method enables the formation of graphics having a gradation of color (e.g. a gradual fade) using both a leuco dye-based composition and a water-soluble ink along with the other components of the article to create the graphics. The present invention also relates to a novel method of forming a color-fill effect graphic for use in absorbent articles. Prior to describing these aspects of the present invention in detail, the following are definitions of various terms.

The term "active graphic" as used herein refers to an appearing graphic, a fading graphic, a color changing graphic or a combination thereof that is formed by a moisture-reacting composition. The term "appearing graphic" is used herein to refer to a graphic that becomes visible (appears) or becomes significantly more visible when exposed to moisture. Conversely, the term "fading graphic" is used herein to refer to a graphic that becomes invisible (disappears) or significantly less visible when exposed to moisture, such as urine, fecal matter, a vaginal secretion or a nasal discharge as occurs with absorbent articles. Conversely, the term "permanent graphic" is used herein to refer to a graphic that does not substantially change its degree of visibility or appearance when exposed to moisture.

In providing the desired aesthetic and/or functional benefits of the article being used, the graphic image may provide a story line involving a permanent character graphic and an active object graphic. The term "character graphic" is used herein to refer to a graphic containing an anthropomorphous image, and in particular an image having or suggesting human form or appearance which ascribes human motivations, characteristics or behavior to inanimate objects, animals, natural phenomena, cartoon characters, or the like. The character graphics may include permanent graphics, active graphics or both permanent and active graphics.

In general, absorbent articles including the multiple layer material of the present invention or formed using the methods of the present invention may contain graphics including multiple images, objects and/or characters. All of the graphics may be assembled together on the absorbent article so as to present an integrated look that depicts a scene. In addition to characters and other images as described above, the scene may include a framing device, outlines, a background, a foreground and one or more silhouettes. A "framing device" generally refers to a substantially continuous border for enclosing an image. The framing device may, for instance, completely surround a single image or multiple images or may substantially surround an image (such as at least about 90% surrounded). The framing device may also intersect the active graphics. For instance, the framing device may substantially surround one active graphic while intersecting another active graphic. A product may contain a single framing device or multiple framing devices. The framing device is made from graphics or from white space and may itself include an object or be part of a larger image or character. An "outline", on the other hand, refers to the lines by which the essential features or main aspects of an image, object or character is defined or bound. In one aspect, for instance, a character appearing on an absorbent article may include an outline made from permanent graphics or from white space. Within the outline, the character may be colored using active graphics.

As used herein, the "background" of a scene is the surface against which represented objects and forms are perceived or depicted. The background is situated behind the location of an image or object. Each scene includes a background. In addition, various elements within the scene may also include a background. As used herein, the "foreground" describes the location of an image or object which is situated in front of something. As understood by one skilled in the art, an object may be both in the foreground and the background.

A "silhouette" is a representation of the general shape of an object, image or character without the essential features or main aspects of the object filled in. The silhouette, for instance, excludes the graphic details or elements intended to show the dimensionality or recognition of the image or character such as facial features, clothing details, flower petals, and the like. A silhouette may also comprise a dark image outlined against a lighter background or vice versa.

Each of the framing device, background, silhouette and other images, objects and characters are graphic elements. An individual absorbent article may have one or more graphic elements.

In one aspect, the present invention relates to a multiple layer material such as may be used as a component of an absorbent article. For example, a multiple layer material may be used to form the outer cover of an absorbent article. The multiple layer material of the invention includes a film layer, a moisture-reacting composition layer and an adhesive layer. The film layer is generally planar and has two surfaces; one or both of those generally planar surfaces is a printed surface. The printing on the printed surface of the film layer may cover a small percentage of the surface or it may cover the entire surface. The moisture-reacting composition layer is adjacent the printed surface of the film layer; the two layers may become adjacent to each other by the moisture-reacting composition layer being printed onto the film layer. A portion of the moisture-reacting composition layer forms a framing device. The moisture-reacting composition layer may form other graphic elements in addition to the framing device. The graphic elements may be purely decorative or aesthetic, they may be functional (e.g. communicate a message) or both. The moisture-reacting composition layer is formed by an ink or dye composition that changes in appearance when it is exposed to moisture (e.g. the moisture being absorbed by the fluid targeted to be managed by the absorbent article in which the moisture-reacting composition is used). The adhesive layer is adjacent the portion of the moisture-reacting composition layer forming the framing device. The adjacency of the adhesive layer may be achieved by selective application of the adhesive layer over the framing device. Placement of the adhesive layer over the portion of the moisture-reacting composition layer forming the framing device converts the framing device from an active graphic to a permanent graphic (a graphic that does not change in appearance in response to the presence of moisture). An advantage of this approach is that all of the graphics on the film layer may be printed with one type of dye/ink composition and a portion of the graphics can be inactivated with adhesive which is needed anyway to attach the various components of the absorbent article together. The thickness of the film, moisture-reacting composition and adhesive layers are similar to those already used in absorbent articles. The adhesive layer may only cover a portion of the moisture-reacting composition layer that is formed on the film layer. The portion of the moisture-reacting composition layer that does not have the adhesive layer adjacent to it remains an active graphic.

In another aspect, the present invention relates to a multiple layer material including a film layer, a leuco dye-based composition layer, a water-soluble ink composition layer and an adhesive layer. The multiple layer material may be used to form one or more components of an absorbent article, such as the outer cover component. The film layer is generally planar and has two, planar surfaces; one or both of the planar surfaces is a printed surface. The leuco dye-based composition layer is adjacent the printed surface of the film layer. The leuco dye-based composition layer may be formed adjacent to the printed surface through printing. The leuco dye-based composition layer forms at least one graphic element. The graphic element may be one or more of a framing device, background, silhouette, image, object or character. As with the leuco dye-based composition layer, the water-soluble ink composition layer is adjacent the printed surface of the film layer and forms at least one graphic element. Different visual effects may be achieved by using both a leuco dye-based composition layer and a water-soluble ink composition layer. The adhesive layer is selectively adjacent at least one of the graphic elements. The adhesive layer may be made selectively adjacent to one of the graphic elements (formed by either the leuco dye-based composition or the water-soluble ink composition) by applying the adhesive layer only to the targeted graphic element and not to surrounding elements on the film layer. The selective application of the adhesive layer may be accomplished by registering the placement of the adhesive layer over the placement of the targeted graphic element. More than one graphic element may be selectively covered by the adhesive layer. When a graphic element has the adhesive layer adjacent to it, it is no longer responsive (i.e. "active") to the presence of moisture.

In a further aspect, the present invention relates to a method of forming a gradient effect graphic for use with an absorbent article. For aesthetic and functional purposes, it may be desirable to incorporate graphics into one or more components of an absorbent article. Some graphics may change in appearance in response to the presence of moisture indicating that the article has performed its function of absorbing fluid. A gradient effect graphic has a gradual change in the intensity of one or more colors. For example, the gradient effect graphic may include a gradual fade of one color into another or the gradual fading away of a color. The gradient effect graphic may have a "tie dye" appearance. The method includes a step of providing a film material such as the type of film material that can be used to form the outer cover of the absorbent article. The film material is generally planar (flat) and has two, planar surfaces. At least one surface is a printed surface; the printed surface has a printed surface area. The printed surface area is defined by the outer perimeter (away from the center of the printed surface) that the printed graphics extend to. The method also includes a step of applying a leuco dye-based composition to greater than 30% of the printed surface area of the film material. The leuco dye-based composition is a type of moisture-reacting composition (that changes in visual appearance in response to the presence of moisture). The leuco dye-based composition forms a printed background coloration having its own area (that is something less than 100% but greater than 30% of the printed surface area of the film material). The printed background coloration may have an initial appearance of a visible color or it may be invisible; the appearance of the printed background coloration changes in response to the presence of moisture (i.e. a visible color fades away or a visible color emerges). The method further includes a step of applying a water-soluble ink to less than 25% of the area of printed background coloration. Like the leuco dye-based composition, the water-soluble ink is a moisture-reacting composition that changes in appearance in response to the presence of moisture. The area covered by the water-soluble ink is no more than one-quarter of the area of the printed background coloration; therefore, the water-soluble ink may be applied in a higher concentration over a smaller area (relative to the leuco dye-based composition). In one outcome of the method, the printed background coloration begins as a visible color and the water-soluble ink is concentrated in a relatively small area of the printed background coloration; upon exposure to moisture, the leuco dye-based composition forming the printed background coloration fades out and the water-soluble ink spreads outward. The combination of the two visual changes creates a gradient effect graphic. The performance of both the leuco dye-based composition and the water-soluble ink may be altered by including a distribution layer adjacent the printed surface of the film material. The distribution layer is then situated between the outer cover component and the absorbent core of the absorbent article.

The present invention also relates to a method of forming a color-fill effect graphic for an absorbent article. The method includes a step of providing a film material. The film material has an exterior-facing surface and an interior-facing surface. The exterior-facing surface of the film material faces away from the absorbent core of the absorbent article and the interior-facing surface faces toward the absorbent core. The method also includes a step of printing an outline graphic on the exterior-facing surface of the film material. The outline graphic defines a shape having a boundary. The shape may be a complete image in that the details of the shape are provided within the boundary; for example, if the shape defined by the outline graphic is a flower, inside the boundary of the flower are additional lines to delineate the petals and center of the flower. The boundary is the outermost portion of the outline graphic. The outline graphic may be printed with either a durable ink or a moisture-responsive ink; however, because it is printed on the exterior-facing surface of the film material, the outline graphic is not exposed to moisture. The method further includes a step of printing the interior-facing surface of the film material with a moisture-reacting composition. The moisture-reacting composition is printed at a location that is opposite the boundary of the shape on the exterior-facing surface. The moisture-reacting composition covers at least 10% of the boundary. By covering at least 10% of the boundary, the moisture-reacting composition can create a color-fill effect graphic that is visible within the boundary of the shape (when looking at the absorbent article from the exterior). If the moisture-reacting composition is printed beyond the boundary of the shape (either by accident or for efficiency), the appearance of the color-fill effect graphic from the exterior of the absorbent article is that the color is filling in (or changing) within the boundary of the shape. The method of the invention also includes a step of providing a distribution layer adjacent the interior-facing surface of the film material. Depending on selection of the material to form the distribution layer, the intensity and clarity of the color-fill effect graphic may be improved. Further, the method includes a step of attaching the distribution layer to the interior-facing surface of the film material using an adhesive. As with selection of the material to form the distribution layer, the quality of the color-fill effect graphic may be improved depending on placement of the adhesive.

Other features and aspects of the present disclosure are discussed in greater detail below.

BRIEF DESCRIPTION OF THE DRAWINGS

The patent or application file contains at least one drawing executed in color. Copies of this patent application publication with color drawing(s) will be provided by the Office upon request and payment of the necessary fee.

A full and enabling disclosure of the present invention, including the best mode thereof to one skilled in the art, is set forth more particularly in the remainder of the specification, including reference to the accompanying figures, in which:

FIG. 3 representatively shows another approach to forming a color-fill effect graphic.

Figure 1A:
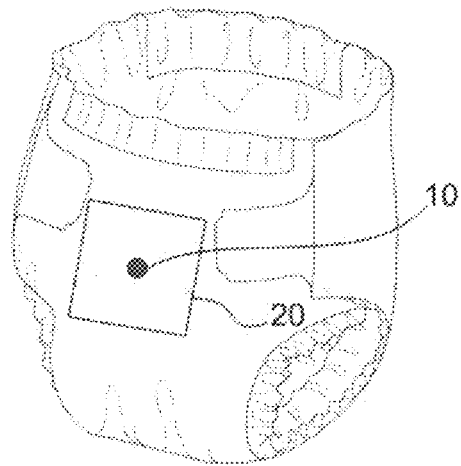
FIGS. 1A-1D are representative images of absorbent articles incorporating the multiple layer material of the invention and showing the appearance of the multiple layer material "before" exposure to moisture (FIG. 1A and FIG. 1C) and after exposure to moisture (FIG. 1B and FIG. 1D) to form a gradient effect graphic.
Figure 1B:
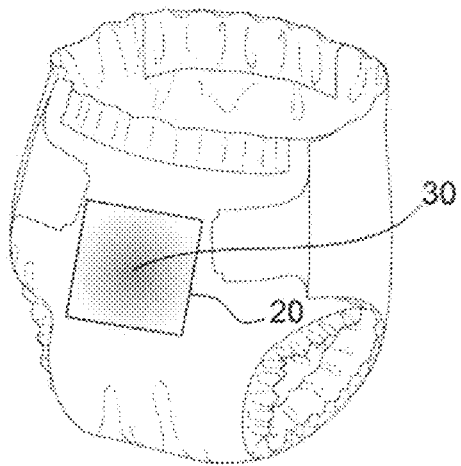

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

In one aspect, the present invention is directed to a multiple layer material that includes a film layer, a moisture-reacting composition layer and an adhesive layer. The film layer is formed to be relatively thin (like a sheet of paper) and is, therefore, generally planar and has two planar surfaces. At least one of those planar surfaces is a printed surface. The film layer may include a thin film material, such as a polyethylene or polypropylene film material. Such polyethylene and polypropylene film materials are of the type typically used to form the outer cover component of an absorbent article. Alternately, the film layer may be formed of a nonwoven material (e.g. spunbond or a spunbond-meltblow-spunbond composite); if desired, the nonwoven material may have barrier properties (to prevent the flow of liquid and, if desired, vapor). The film layer may be "permeable" or "impermeable" to vapor and liquid. With typical executions of diapers with breathable outer covers, the film layer is vapor permeable but impermeable to liquid. As stated above, the film layer is generally planar (that is, two-dimensional because of its low thickness) and it may be elastic. Being elastic may mean that the film layer is stretchable in one or both planar directions. If it is desirable for the film layer to have elastic properties, the film layer may be made from block copolymers, such as styrene-ethylene-butylene-styrene or styrene-isoprene-styrene block copolymers. With the multiple layer material of the invention, the film layer includes at least one printed surface and, if desired, both surfaces may be printed. It is not necessary for the entire surface of either side of the film layer to be printed; that is, portions of one or both surfaces may be printed.

The printing of the printed surface may be formed through traditional printing techniques such as offset, rotogravure, flexography, screen, digital, ink jet and laser. The printed surface may be completely or partially printed with patterns, words and/or graphics. The printed surface may be printed with one or more ink or other compositions suitable for forming the desired patterns, words or graphics. The ink compositions may form one or more graphic elements such as framing devices, backgrounds, silhouettes and other images, objects and characters. At least a portion of the printed surface is printed with the moisture-reacting composition layer such that the moisture-reacting composition layer is adjacent the printed surface. The moisture-reacting composition layer may be formed by any of the color inks or dyes known in the art for changing appearance in response to exposure to moisture ("moisture" means fluids that contain some amount water). The change in appearance may occur as one or more of the following: fading of same color, disappearance of color to give a "clear" appearance, appearance of color from a "clear" appearance, spreading of color and/or change from one color to another. Examples of moisture-reacting compositions suitable for forming the layer on the printed surface are well-known. For example, U.S. Pat. No. 4,022,211 issued to Timmons et al. describes "coloring agents" that can be used to form decorative patterns on various components of a diaper. The patterns may be formed by permanent coloring agents and/or by water-dispersible coloring agents. One example of a water-dispersible coloring agent provided in the Timmons et al. patent is formulated from a 50% solution of polyvinyl alcohol and 0.1% by weight of a colored dye. The polyvinyl alcohol solution acts as a binder to apply and affix the colored dye or pigment to the printed surface of the film layer. Examples of other suitable water-dispersible or water-soluble binders include modified cellulosics such as carboxymethyl cellulose, cellulose glycolate and other forms of methyl cellulose and glycol cellulose. Gelatins, gums, starches, dextrins and various sugars may also be used as binders and may be selected based on compatibility with the desired colored dye or pigment. Generally speaking, the "coloring agents" of the Timmons et al. patent which can be used as moisture-reacting compositions in the present invention disperse and/or fade in response to exposure to moisture. The subject matter of the Timmons et al. patent is incorporated herein. The compositions of the Timmons et al. patent are examples of moisture-reacting compositions that may be referred to as water-soluble ink compositions.

Another example of a suitable moisture-reacting composition is a composition that includes a matrix-forming component, a colorant, a surfactant and a pH adjuster. Moisture-reacting compositions of this type are described in U.S. patent application Ser. No. 12/825,877 filed on Jun. 29, 2010; the content of application Ser. No. 12/825,877 ("the '877 application") is hereby incorporated by reference. In summary, the matrix-forming component of the '877 application can be a water-insoluble, film-forming polymer or an ink base, such as a flexographic varnish having an organic solvent base. The colorant can be a pH indicator, preferably a charged pH indicator, capable of changing color in response to the presence of moisture. The surfactant includes a charged surfactant that attracts the colorant or a combination of a charged surfactant that attracts the colorant and a neutral surfactant. The pH adjuster may include a low molecular weight organic acid and a high molecular weight organic acid. The moisture-reacting composition is fluid at room temperature and may be applied as an ink to the printed surface, such as by printing, spraying or stamping. The moisture-reacting composition may be dissolved in an organic solvent that acts as a carrier and later evaporates after the moisture-reacting composition is applied to the printed surface. The matrix-forming component of the moisture-reacting composition can include one or more water-insoluble, film-forming polymers and/or one or more ink bases, such as a flexographic varnish having an organic solvent base. In part, the function of the matrix-forming component is to keep the surfactant, colorant and pH adjuster in proximity to each other. The water-insoluble, film-forming polymer may be selected from acrylate/acrylamide copolymers, polyurethane adhesives, methylcellulose and copolymers of vinylpyrrolidone and dimethylaminopropyl methacrylamide.

The matrix-forming component may also or alternatively include an ink base material. The ink base material may include a small molecule, a polymeric material or a mixture of small molecules and polymers. Examples of suitable small molecule base materials include glycols, including triglycerols and their derivatives. Examples of suitable polymeric materials that may be used as ink base materials include polyvinyl alcohol, polyvinyl pyrrolidone, polyethylene glycol, water-insoluble derivatives of polyacrylates and polyacrylamides, poly(hydroxyethyl methacrylates), poly(hydroxylethyl acrylates), carboxymethyl cellulose, gelatin and gum Arabic. Another suitable ink base material for the moisture-reacting compositions of the invention is a flexographic varnish base such as a nitrocellulose compound based varnish or a phenolic-modified co-solvent-type polyamide resin-based varnish.

The surfactant of the moisture-reacting composition may be either a charged surfactant that attracts the colorant or a combination of a charged surfactant that attracts the colorant and a neutral surfactant. When the surfactant is charged, the surfactant increases the wettability of the moisture-reacting composition and helps reduce the leaching of the oppositely-charged colorant. The colorant may be a pH indicator where the pH indicator is selected from bromocresol green, bromophenol blue and bromochlorophenol blue. The colorant may be selected so that it responds by changing color to a particular physical or chemical condition. If a charged colorant and an oppositely charged surfactant are used (because the colorant is bound to the surfactant), the colorant is stabilized and is less likely to leach away from the moisture-reacting composition. The moisture-reacting composition may include one or more colorants. When more than one charged colorant is used, the charged colorants may be selected based on the desired effect (e.g. different color, better visibility, etc.). The colorant may include a polymeric colorant. The polymeric colorant can be a charged and/or neutral polymeric pH indicator.

A possible execution of the present invention includes a film layer that is a breathable outer cover of an absorbent article where the breathable outer cover includes calcium carbonate. For such executions, the pH adjuster includes from 1% to 20% of a low molecular weight organic acid and from 1% to 20% of a high molecular weight organic acid. It is believed that the combination of low molecular weight and high molecular weight organic acids prevents premature color change by the charged colorant caused by contact with the calcium carbonate in the breathable outer cover (that the film layer is a component of). The pH adjuster may include a ratio of 0.02 to 50 of low molecular weight organic acid to high molecular weight organic acid. The moisture-reacting composition of the type described in the '877 application generally includes 20% to 95% of a matrix-forming component; 0.1% to 10% of a colorant; 2% to 50% of a surfactant; and 0.1% to 20% of a pH adjuster, wherein the pH adjuster includes a low molecular weight organic acid and a high molecular weight organic acid. As used as part of the multiple layer material of the present invention, the compositions of the '877 application generally experience a change in appearance in response to moisture of one color to a different color (e.g. from blue in appearance to yellow).

Another example of a composition that can be used as a moisture-reacting composition with the present invention is described in U.S. Patent Application Ser. No. 61/419,981 ("the '981 application"), filed as a provisional application on Dec. 6, 2010; the content of the '981 application is incorporated herein. The moisture-reacting composition of the '981 application is a homogenous composition that includes a matrix-forming component, a leuco dye, a Lewis Acid, a neutral surfactant and an organic solvent. The matrix-forming component can be a water-insoluble, film-forming polymer or an ink base, such as a varnish having an organic solvent base. The leuco dye may be selected from phthalide type or fluoran type dyes. The Lewis Acid may be a metal salt-based Lewis Acid. The neutral surfactant may be a neutral block copolymer surfactant. The composition may be dissolved in an organic solvent. More particularly, the composition of the '981 application contains at least one leuco dye and at least one Lewis Acid. The leuco dye is an electron-donating component and the Lewis Acid is an electron-accepting component. The leuco dye and the Lewis Acid form colored complexes when the color-changing composition is in a dry state. The mechanism for the color to disappear from the composition includes the introduction of an aqueous based liquid (e.g. water or urine) to the composition. The Lewis Acid is more attracted to the water than the leuco dye and the color disappears from the composition. The composition may serve as a moisture indicator by rapidly and distinctly becoming colorless in the presence of moisture as the Lewis Acid becomes more attracted to the water and disassociates from the leuco dye.

The matrix-forming component of the composition can include one or more water-insoluble, film-forming polymers and/or one or more ink bases, such as a varnish having an organic solvent base. In part, the functions of the matrix-forming component are to provide a binding matrix to keep other components of the composition, such as the surfactant, leuco dye and Lewis Acid, from significant leaching when wetted and to provide a suitable viscosity required for printing. Benefits of the composition including a film-forming polymer include that the composition adheres effectively to the film layer which prevents the composition from cracking off of the film layer when the composition is dry. The colored complex is less likely to leach away from or out of the composition in the presence of water or urine when the water-insoluble polymers and/or varnishes are included in the composition. The matrix-forming component may also or alternatively include an ink base material. The ink base material may include a small molecule, a polymeric material or a mixture of small molecules and polymers. Another suitable ink base material for the compositions of the '981 application is a varnish base such as a nitrocellulose compound-based varnish, ethyl cellulose-based varnish, polyurethane-based binding systems or a phenolic-modified co-solvent-type polyamide resin-based varnish. It is believed that the ink base material may help the stability of the composition in forming the moisture-reacting composition layer on the printed layer. It is also believed that the ink base material may improve the adhesion of the composition to the film layer. The ink base material may be water-insoluble.

The neutral surfactant in the compositions of the '981 application can be a neutral block copolymer surfactant comprising blocks of two different poly(alkylene oxides). These neutral block copolymer surfactants can be selected from polyoxypropylene-polyoxyethylene block copolymer, poly[poly(ethylene oxide)-block-poly(propylene oxide)] copolymer or propylene glycol-ethylene glycol block copolymer. The neutral block copolymer acts as a wettability agent and provides good solubility in both alcohol-based solvents and water. The leuco dye may be selected so that it responds by changing color to a particular physical or chemical condition. The charged leuco dye forms a colored complex with the oppositely charged Lewis Acid. The colored complex of leuco dye and Lewis Acid is not significantly affected by the neutral surfactant as opposed to if a charged surfactant were used in the composition. The neutral surfactant preserves the leuco dye/Lewis Acid colored complex—and provides good wettability without a significant reduction in color intensity. A charged surfactant significantly reduces the color intensity by negatively impacting the formation of the complex of leuco dye and the Lewis Acid in the composition. With the compositions of the '981 application, the compositions generally include the following proportions of components: 20% to 95% of the matrix-forming component; 0.1% to 10% of the leuco dye; 1% to 20% of the Lewis Acid; and 2% to 50% of the neutral surfactant.

As described herein, the moisture-reacting composition layer is provided (by printing or otherwise) adjacent the printed surface of the film layer. A portion of the moisture-reacting composition layer forms a framing device. The multiple layer material of the invention also includes an adhesive layer that is adjacent the portion of the moisture-reacting composition layer forming the framing device. The adhesive layer may also be applied over other portions of the moisture-reacting composition layer. The adhesive layer may cover the moisture-reacting composition layer in its entirety or it may only cover a portion of the moisture-reacting composition layer. While adhesive has generally been found to interfere with the performance of moisture-sensitive ink compositions used to form graphics on absorbent articles, the adhesive can be used to improve graphic performance. For example, as encompassed by the present invention, the adhesive layer can be applied over the moisture-reacting composition layer to make the color component of the moisture-reacting composition layer unaffected by moisture. This construction provides the benefit of using a single moisture-reacting composition to form both the "active" and "permanent" graphics within a product, such as an absorbent article. Hence, the adhesive layer is selectively applied over the portions of the moisture-reacting composition layer for which a "permanent" graphic effect is desired, such as the framing device. The adhesive layer may be formed of known adhesives for attaching the components of an absorbent article together. For example, a suitable adhesive is the adhesive sold under the trade name "H9574-A" by Bostik, Inc. of Wauwatosa, Wis. Other suitable adhesives include those sold under the trade names "34-5610" and "34-5611" available from the Henkel Corporation and "RT-8723" available from REXtac, LLC located in Odessa, Tex. The adhesive layer may include adhesives that are elastic or inelastic; the elasticity of the adhesive may be selected depending on the desired finish product properties. Examples of suitable elastic adhesives include those sold under the trade names "H20030" by Bostik, Inc. and "EL5398" by Henkel Corporation. The adhesive may be applied to the film layer and moisture-reacting composition layer of the invention in different patterns. For example, the adhesive may be applied in a swirl pattern and the size of the swirls may be varied. Additional adhesive patterns include the pattern formed by random spray application of the adhesive and the pattern of a consistent coating formed by slot coat application of the adhesive. Further, the adhesive may be applied selectively using known registration technology. For example, it may be desirable for the adhesive layer to be applied to be registered with particular sections or portions of the moisture-reacting composition layer. It may also be desirable for the adhesive layer to be selectively applied to be adjacent specific graphic elements of the total combination of graphics formed on the film layer. "Selectively applied" means that the adhesive is applied to the desired graphic elements, but not to the portion of the film layer surrounding the desired graphic elements or to other graphic elements formed by a moisture-reacting composition layer in proximity to the desired graphic elements. The effect of the adhesive layer being registered with particular graphic effects is that those graphic effects will be rendered "permanent" or "inactive" and will no longer change in appearance in response to the presence of moisture. In another aspect, the film layer may be printed with both a leuco dye-based composition layer and a water-soluble ink composition layer adjacent the printed surface. Each of the leuco dye-based composition layer and the water-soluble ink composition layer may form a graphic element. The adhesive layer may then be selectively adjacent to at least one of the graphic elements formed by the two types of moisture-reacting compositions. When a graphic element is covered with the adhesive layer, the adhesive layer has the effect of changing the graphic element from an "active" to a "permanent" graphic.

In another aspect, the present invention relates to a method of forming a gradient effect graphic for an absorbent article. The "gradient effect" refers to a dispersion of an ink in which the ink color is most intense in the center with a gradual decrease in intensity of color as the radial distance increases from the center at which the ink composition was initially placed. The intensity of color at a center point is achieved by applying an increased concentration of the ink in a central location. When the ink is exposed to moisture, the gradient effect forms as the ink is carried away from the center point by fluid transport with the moisture across the film material to which the ink is applied. The increased concentration of the ink at the center point decreases as ink particles are transported away from the center point with the moisture. The gradient of ink particle concentration also creates a visual gradient of color. When two different colors of ink are placed near each other and the gradient effect occurs, the gradient effect may look similar to a "tie dye" effect used to decorate articles of clothing. In the case of use of a gradient effect graphic with an absorbent article, the graphic is activated and the gradient effect forms when the absorbent article is exposed to moisture.

Looking at the photograph of FIG. 1, FIG. 1A depicts an example of the graphic elements needed for formation of a gradient effect graphic. FIG. 1A includes a framing device 20 within which a concentrated ink area 10 is placed. FIG. 1A illustrates the appearance of the framing device 20 and the concentrated ink area 10 prior to exposure to moisture. In the context of an absorbent article, the framing device 20 may be printed on the film material of the article's outer cover on either the inward or outward facing surface of the film material. The framing device 20 may be formed of an ink composition that is unresponsive to the presence of moisture. For example, the framing device 20 may be formed with a non-water soluble ink such that the framing device 20 does not change in appearance when the film material is exposed to moisture and wetness from the absorbent core of the article. Alternatively, to achieve printing process efficiency, the framing device 20 may be formed of a moisture-reacting composition, as described herein, where the moisture-reacting composition is printed over with an adhesive layer—thereby rendering the moisture-reacting composition unresponsive to the presence of moisture. The framing device 20 may be formed in a variety of shapes including a shape that forms a decorative graphic; the shape may be a basic shape such as a square or circle or the framing device 20 may be in a shape that represents an outline of an object such as a flower, car, star, dress, etc. The concentrated ink area 10 is placed within the framing device 20 at a location from which dispersion of the color of the ink is desired. The color associated with the concentrated ink area 10 will generally radiate outward when the concentrated ink area 10 is exposed to moisture. The concentrated ink area 10 is formed of a moisture-reacting composition layer that is adjacent the printed surface of the film layer that forms part of the outer cover of the absorbent article. The moisture-reacting composition layer forming the concentrated ink area 10 is without an adhesive layer adjacent to it. Depending how the framing device 20 is formed, the framing device 20 may or may not contain the dispersion of color that occurs when the concentrated ink area 10 is exposed to moisture. Depending on the type of gradient effect graphic desired, the framing device 20 may enclose more than one concentrated ink area 10 and the concentrated ink areas 10 may be different colors. FIG. 1B illustrates the appearance of the gradient effect graphic 30 formed because the concentrated ink area 10 was exposed to moisture. The change in appearance of the concentrated ink area 10 to the gradient effect graphic 30 in response to exposure to moisture categorizes the concentrated ink area 10 as an active graphic. An active graphic can serve one or more purposes in addition to an aesthetic visual effect. For example, a purpose of a change in appearance of an active graphic on an absorbent article may be to indicate occurrence of a fluid insult or the magnitude/frequency of fluid insults. The change in appearance of the active graphic may also indicate a change in physiological condition. A combination of one or more concentrated ink areas 10 formed of one or more colors may form a gradient effect graphic 30 conveying a desired aesthetic appearance such as a certain combination of blended colors or a desired resulting shape effect. The final aesthetic appearance of the gradient effect graphic 30 after exposure to moisture may or may not be combined with the framing device 20 to form an overall visual effect. The decorative graphic including a combination of the framing device 20 and the gradient effect graphic 30 may be formed on either the inward (interior) facing or outward (exterior) facing surface of the film layer constituting a component of the outer cover of an absorbent article.

The vibrancy and color intensity of the gradient effect graphic 30 formed in response to the presence of moisture is affected by the placement of the adhesive layer. Placement of the adhesive layer adjacent the moisture-reacting composition layer will prevent the moisture-reacting composition layer from changing in visual appearance in response to the presence of moisture.

When used as a component of an absorbent article, the performance of the multiple layer material of the invention is affected by the other components of the absorbent article that are in physical proximity to the multiple layer material. For example, when the multiple layer material is used as part of the outer cover of the absorbent article, performance of the multiple layer material is affected by the absorbent core of the article and any components located between the outer cover and the absorbent core. With some absorbent articles, there is a distribution layer located between the outer cover and the absorbent core. The distribution layer may be made of a polymeric nonwoven material, such as a spunbond material or a spunbond-meltblown-spunbond material, or of a tissue material made from paper fibers. The distribution layer facilitates movement of the moisture across the full area of the absorbent core and it also provides a barrier between the absorbent core (which may be loaded with fluid) and the outer cover. The barrier effect reduces a damp feeling on the exterior of the outer cover when the film layer of the outer cover is "breathable" ("breathable" meaning the outer cover allows dissipation of moisture in the form of vapor but not in the form of a liquid).

With the moisture-reacting composition layers of the invention, the presence or absence of a distribution layer and the type of material used to form the distribution layer impact the intensity and how dramatic of an effect is produced when the moisture-reacting composition layer changes color. For example, when the distribution layer is formed of a tissue material, such as a 16.6 gsm White Forming Tissue available from Cellu Tissue Holdings, Inc., there is a positive effect on the speed with which the moisture-reacting composition layer responds to the presence of moisture; further, the appearance of the response is improved. For example, there is a clear distinction between the appearance of the moisture-reacting composition layer prior to exposure to moisture and after exposure to moisture. When the distribution layer is formed of a hydrophilic spunbond-meltblown-spunbond ("SMS") nonwoven material, the quality (e.g. definition, color intensity, speed, etc.) of the change in appearance of the moisture-reacting composition layer can be positively impacted by using increased levels of a wettable surfactant treatment on the SMS, reducing the meltblown percentage in relation to the spunbond percentage and reducing the overall basis weight of the SMS composite. Improved speed and color intensity were observed in the moisture-reacting composition's response to moisture with distribution layers formed of SMS having basis weights of 8 grams/$m^2$ and 10 grams/$m^2$ versus a distribution layer formed of SMS having a basis weight of 11 grams/$m^2$. Similar improvement was seen when comparing different surfactant treatment levels on SMS materials having different percentages of meltblown. In another evaluation, two samples of SMS material, both having a basis weight of 10 grams/$m^2$, but one sample being 80% spunbond/20% meltblown and the other sample being 90% spunbond/10% meltblown were tested. Another variable (besides meltblown %) was the treatment level of surfactant; samples of each type of SMS material were treated with surfactant at levels of 0.5% and 0.65% (the % levels represent the amount of "active ingredient" in the total treatment composition that is applied to the SMS material). The samples having the lower percentage (10%) of meltblown had a positive impact on the change in appearance of the moisture-reacting composition, as did the higher treatment level of surfactant (0.65%). The observations were based on the distribution layer completely covering the surface of the absorbent core facing the film layer material of the outer cover.

Figure 1C:
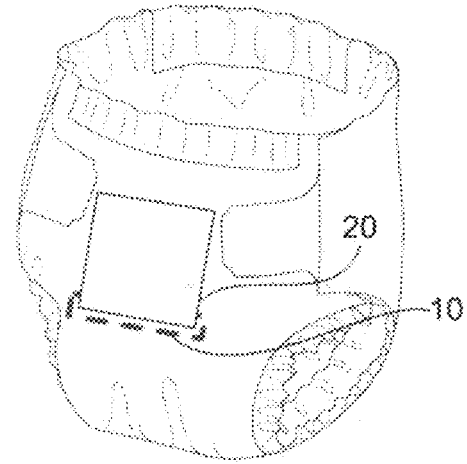
Figure 1D:
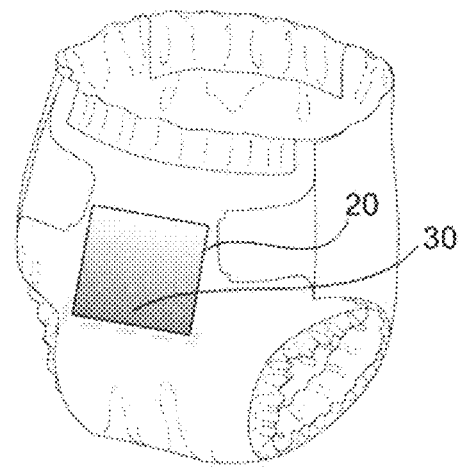

FIGS. 1C and 1D representatively illustrate a different execution to form the gradient effect graphic 30. In FIG. 1C, the framing device 20 is formed as previously described, but the concentrated ink area 10 is in the form of a dashed line. The dashed line is approximately in the shape of a rectangular outline situated at the lower end of the framing device 20. While FIG. 1C illustrates the appearance of the framing device 20 and the concentrated ink area 10 before exposure to moisture, FIG. 1D illustrates the appearance after exposure to moisture. The concentrated ink area 10 fades to form the gradient effect graphic 30. The fluid transport of the moisture carries the ink particles away from the concentrated ink area 10. As shown in FIG. 10, the color remains most concentrated and intense in the area closest to the concentrated ink area 10 and the color gradually fades and decreases in intensity as distance away from the concentrated ink area 10 increases.

In another aspect, the present invention relates to a method of forming a color-fill effect graphic for an absorbent article. The "color-fill effect" refers to an appearance of ink to fill a defined ("framed") area and/or a disappearance of ink from a defined area. One or more inks either appear or disappear in response to the presence of moisture. The appearance/disappearance of ink is a color change in response to moisture. As already described herein, selected inks are able to change in appearance upon exposure to moisture as follows: (1) change from visible color to a "clear" appearance; (2) change from a "clear" appearance to a visible color; and (3) change from one visible color to a different visible color. When the color-fill effect graphic is used within an absorbent article, the graphic is activated and the color-fill effect graphic forms when the absorbent article is exposed to moisture.

Figure 2A:
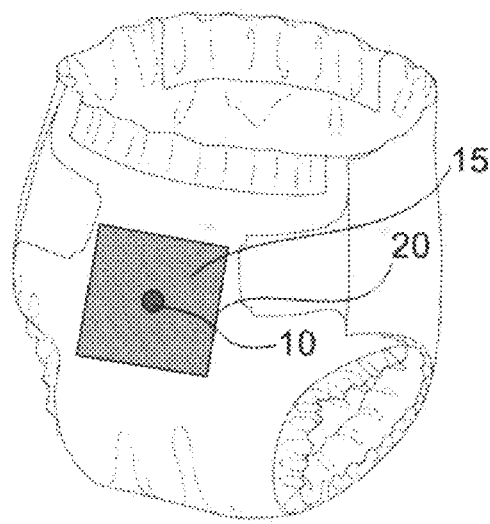
FIGS. 2A-2D are representative images of absorbent articles incorporating the multiple layer material of the invention and showing the appearance of the multiple layer material "before" exposure to moisture (FIG. 2A and FIG. 2C) and after exposure to moisture (FIG. 2B and FIG. 2D to form a color-fill effect graphic.

Looking at the photograph of FIG. 2, FIG. 2A representatively depicts an example of the graphic elements needed to form a color-fill effect graphic 40. FIG. 2A includes a framing device 20 within which there is a solid ink area 15 and a concentrated ink area 10. FIG. 2A illustrates the appearance of these elements prior to exposure to moisture. In the context of an absorbent article, the framing device 20 may be printed on either the inward (interior) or outward (exterior) facing surface of the film material of the article's outer cover. The framing device 20 may be formed of an ink composition that is unresponsive to the presence of moisture. For example, the framing device 20 may be formed with a non-water soluble ink such that the framing device 20 does not change in appearance when the film material is exposed to moisture and wetness from the absorbent core of the article. Alternatively, to achieve printing process efficiency, the framing device 20 may be formed of a moisture-reacting composition, as described herein, where the moisture-reacting composition is printed over with an adhesive layer—thereby rendering the moisture-reacting composition unresponsive to the presence of moisture. The framing device 20 may be formed in a variety of shapes, including a shape that forms a decorative graphic; the shape may be a basic shape such as a square or circle or the framing device 20 may be in a shape that represents an outline of an object such as a flower, car, star, dress, etc. In FIG. 2A, the concentrated ink area 10 is shown as being approximately in the center of the framing device 20, though the concentrated ink area 10 could be anywhere within the framing device 20. The concentrated ink area 10 is formed of a moisture-reacting composition layer that is adjacent the printed surface of the film layer that forms part of the outer cover of the absorbent article. The moisture-reacting composition layer forming the concentrated ink area 10 is without an adhesive layer adjacent to it. Depending on the type of color-fill effect desired, there may be more than one concentrated ink area 10 and the areas 10 may be of different visible colors.

Figure 2B:
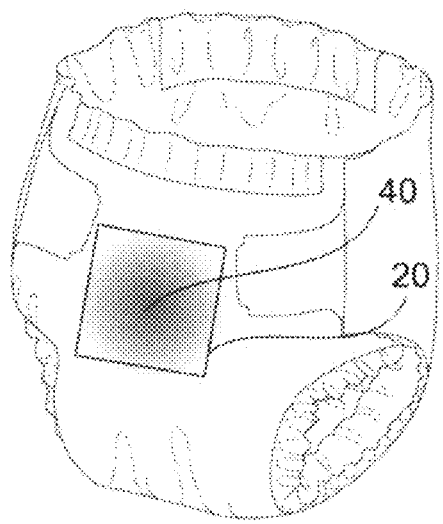

FIG. 2B illustrates the appearance of the article shown in FIG. 2A after exposure to moisture. In FIG. 2B, the visible color of the solid ink area 15 has "disappeared"; i.e. the solid ink area 15 changed from a visible color to colorless with exposure to moisture. Also in FIG. 2B, the concentrated ink area 10 has radiated outward from the center point of its location to color-fill the area within the framing device 20. In this example, the concentrated ink area 10 has not changed color, but has maintained its color and has dispersed outward. As with the example of the gradient effect graphic 30 illustrated in FIG. 1, the color-fill effect graphic 40 of FIG. 2 is an active graphic.

Figure 2C:
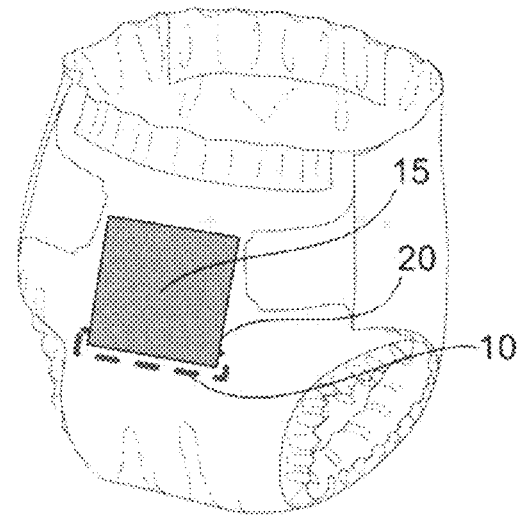
Figure 2D:
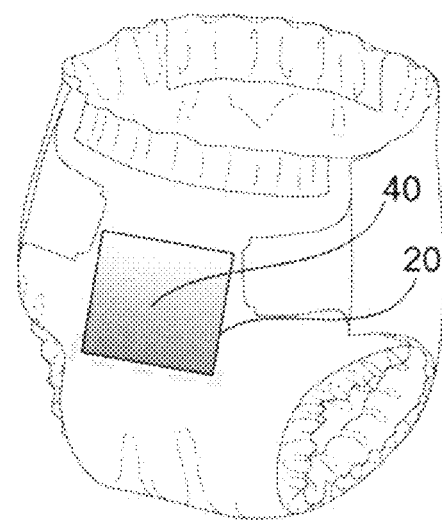

FIGS. 2C and 2D illustrate the "before" and "after" exposure to moisture for a different execution to form the color-fill effect graphic 40. In FIG. 2C, the framing device 20 is formed as previously described, but the concentrated ink area 10 is in the form of a dashed line. The solid ink area 15 is in the same configuration as it was in FIG. 2A. The dashed line is approximately in the shape of a rectangular outline situated at the lower end of the framing device 20. FIG. 2D shows the appearance of the article depicted in FIG. 2C after exposure to moisture. As with the first example of the color-fill graphic effect, the solid ink area 15 has changed from a visible color to colorless. The concentrated ink area 10 has dispersed in response to the presence of moisture to fill color within the framing device 20. Though the concentrated ink area 10 does not change color to form the color-fill effect graphic, it could have changed color in response to the presence of moisture.

As previously described herein, the quality of the color-fill effect graphic is impacted by the selection of the materials used to form the other components of the article within which the color-fill effect graphic is being used. For example, the quality of the color-fill effect graphic may be impacted by whether there is a distribution layer and the material used to form the distribution layer. Certain materials, such as tissue material, have been found to improve the quality/appearance of the color-fill graphic effect. The improvements include more distinctive change between "before" and "after" exposure to moisture and better color intensity.

Figure 3B:
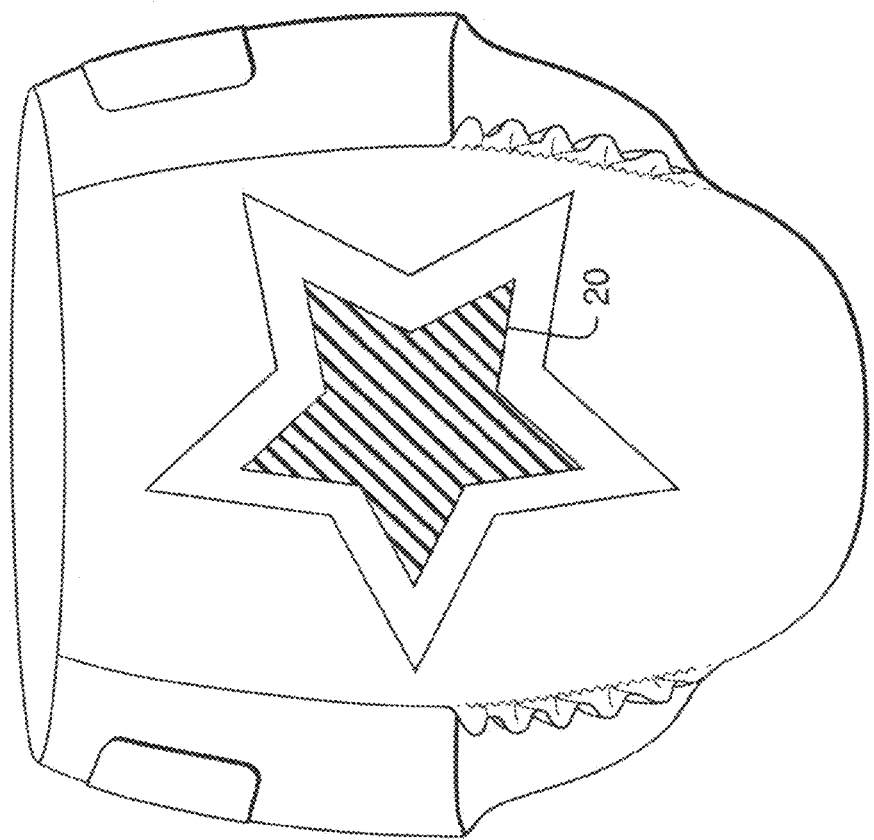
FIG. 3 is a representative drawing of an absorbent article incorporating the multiple layer material of the invention.
FIG. 3A shows the absorbent article "before" exposure to moisture and FIG. 3B shows the absorbent article "after" exposure to moisture.
Figure 3A:
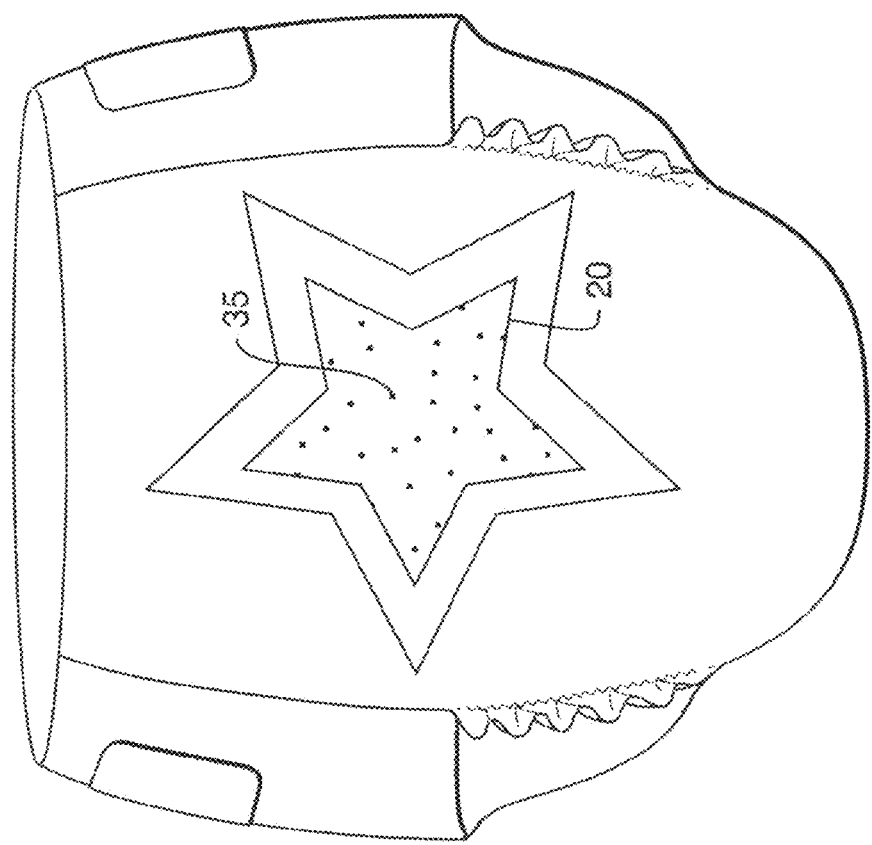

FIG. 3 shows another representative example of a color-fill effect graphic for an absorbent article of the invention. FIG. 3A shows the appearance of the graphic on the absorbent article before exposure to moisture and FIG. 3B shows the appearance of the graphic after exposure to moisture. FIG. 3A shows a framing device 20 in the shape of a star, but there is no solid ink area 15. However, the framing device 20 defines an interior filled with a dot pattern of ink 35. The dot pattern of ink 35 gives a visual appearance of the interior of the star-shaped framing device 20 not having a color. In FIG. 3B, after exposure to moisture, the dot pattern of ink 35 has changed in appearance to create the color-fill effect graphic within the framing device 20. The diagonal lines that fill the interior of the star-shaped framing device 20 in FIG. 3B, represent a solid coloration, but do not represent any particular color. After exposure to moisture, the framing device 20 has the visual appearance of being a solid, filled color.

In another aspect, the present invention is directed to a method of forming a gradient effect graphic for an absorbent article including a step of providing a film material. The film material has a printed surface and a printed surface area. The film material has an inward-facing and an outward-facing surface; the printed surface may be on either or both of the inward-(interior) and outward-(exterior) facing surfaces. The printed surface area may be from 0% to 100% of the surface area of the film material. The method also includes a step of applying a lueco dye-based composition to greater than 30% of the printed surface area of the film material to form a printed background coloration having an area. Suitable lueco dye-based compositions include those described herein as moisture-reacting compositions. In order to calculate the area of the printed background coloration, it may be necessary to sum different sub-areas of the film material on which the leuco dye-based composition has been applied; that is, the printed background coloration may not be continuous. Also, if the leuco dye-based composition is applied in a dot pattern, the approximate area of an individual dot needs to be multiplied by an estimate of the number of dots. Additionally, the method includes a step of applying a water-soluble ink to less than 25% of the area of the printed background coloration. Suitable water-soluble inks are described herein as examples of moisture-reacting compositions. Examples of water-soluble inks are described in the Timmons et al. patent.

In another aspect, the present invention is directed to a method of forming a color-fill effect graphic for an absorbent article including a step of providing a film material. The film material has an exterior-facing surface and an interior-facing surface. The method also includes a step of printing an outline graphic on the exterior-facing surface of the film material. The outline graphic may be formed of any type of ink (water insoluble, water soluble or water soluble printed over with adhesive to render the ink unresponsive to the presence of moisture). The outline graphic defines a shape having a boundary. Additionally, the method includes a step of printing the interior-facing surface of the film material with a moisture-reacting composition at a location that is opposite the boundary of the shape. The moisture-reacting composition covers at least 10% of the boundary of the shape (on the opposite surface of the film material). The method of the invention further includes a step of providing a distribution layer adjacent the interior-facing surface of the film material. The distribution layer may partially or entirely surround the absorbent core of the absorbent article and may be formed of a nonwoven layer (e.g. spunbond material or fibrous, tissue material). As described herein, the presence of and material selection for the distribution layer impacts the quality of the appearance of the color-fill graphic effect. The method also includes a step of attaching the distribution layer to the interior-facing surface of the film material using a construction adhesive.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A multiple layer material comprising:
   a film layer, wherein the film layer has a printed surface;
   a leuco dye-based composition layer, wherein the leuco dye-based composition layer is adjacent the printed surface of the film layer and wherein the leuco dye-based composition layer forms at least one graphic element;
   a water-soluble ink composition layer, wherein the water-soluble ink composition layer is adjacent the printed surface of the film layer and wherein the water-soluble ink composition layer forms at least one graphic element; and
   an adhesive layer, wherein the adhesive layer is selectively adjacent at least one of the graphic elements.

2. The multiple layer material of claim 1 wherein the graphic elements may be selected from framing devices, backgrounds, silhouettes, objects, images and characters.

3. The multiple layer material of claim 1 wherein the adhesive layer is registered with a graphic element.

4. A method of forming a gradient effect graphic for an absorbent article comprising the steps of:
   a. Providing a film material, wherein the film material has a printed surface and a printed surface area;
   b. Applying a leuco dye-based composition to greater than 30% of the printed surface area of the film material to form a printed background coloration having an area; and
   c. Applying a water-soluble ink to less than 25% of the area of the printed background coloration.

5. The method of forming a gradient effect graphic for an absorbent article of claim 4 further comprising a step of providing a distribution layer adjacent the printed surface of the film material.

6. A method of forming a color-fill effect graphic for an absorbent article comprising the steps of:
   a. providing a film material, wherein the film material has an exterior-facing surface and an interior-facing surface;
   b. printing an outline graphic on the exterior-facing surface of the film material wherein the outline graphic defines a shape having a boundary;
   c. printing the interior-facing surface of the film material with a moisture-reacting composition at a location that is opposite the boundary of the shape wherein the moisture-reacting composition covers at least 10% of the boundary;
   d. providing a distribution layer adjacent the interior-facing surface of the film material; and
   e. attaching the distribution layer to the interior-facing surface of the film material using an adhesive.

* * * * *